United States Patent [19]

Perry et al.

[11] Patent Number: 4,966,156

[45] Date of Patent: Oct. 30, 1990

[54] PRESSURIZATION SYSTEM FOR CONTINUOUS BLOOD PRESSURE MONITOR TRANSDUCER

[75] Inventors: William D. Perry; Dean C. Winter, both of San Antonio, Tex.

[73] Assignee: Colin Electronics Co., Ltd., Aichi, Japan

[21] Appl. No.: 160,689

[22] Filed: Feb. 25, 1988

[51] Int. Cl.[5] ................................................ A61B 5/02
[52] U.S. Cl. .................................... 128/672; 128/677; 128/687
[58] Field of Search ............... 128/672, 675, 687, 688, 128/689, 690, 4, 677, 678, 679, 680, 681

[56] References Cited

U.S. PATENT DOCUMENTS

| | | | |
|---|---|---|---|
| 3,518,033 | 6/1970 | Anderson | 600/16 |
| 3,585,987 | 6/1971 | Svensson | 128/672 |
| 3,926,179 | 12/1975 | Petzke et al. | 128/672 |
| 4,375,941 | 3/1983 | Child | 600/16 |
| 4,705,034 | 11/1987 | Perkins | 128/204.26 |

Primary Examiner—Max Hindenburg
Assistant Examiner—J. P. Lacyk
Attorney, Agent, or Firm—Oliff & Berridge

[57] ABSTRACT

A pressurization system for a continuous blood pressure monitor transducer. The system comprises dual chamber compression apparatus and a switching mechanism, both of which are engaged with a servo motor drive mechanism. The drive mechanism simultaneously controls the compression apparatus and the switching mechanism, thereby coordinating flow of air from the compression chambers to the pressurizable chamber within the transducer. A detachable connector permits simultaneous interruption of air flow and the control signals to the drive mechanism.

8 Claims, 4 Drawing Sheets

PRESSURIZATION SYSTEM FOR CONTINUOUS BLOOD PRESSURE MONITOR TRANSDUCER

FIELD OF THE INVENTION

The present invention relates generally to a system for continuous noninvasive measurement of blood pressure. More specifically, the present invention provides a means for bring a sensor into contact with a patient's arm to cause optimal flattening of an artery in the arm underlying the sensor, thus allowing a plurality of pressure sensing elements on the sensor to track the actual pulse waveform in the artery and provide an accurate measurement of the patient's blood pressure.

BACKGROUND

There has been considerable interest in recent years in the development of a monitoring system for obtaining a continuous measurement of a patient's blood pressure. One of the most promising techniques for obtaining such a continuous measurement involves the use of an arterial tonometer comprising an array of small pressure sensing elements fabricated in a silicon "chip." The use of such an array of sensor elements for blood pressure measurements is disclosed generally in the following U.S. Pat. Nos. 3,123,068 to R. P. Bigliano, 3,219,035 to G. L. Pressman, P. M. Newgard and John J. Eige, 3,880,145 to E. F. Blick, 4,269,193 to Eckerle, and 4,423,738 to P. M. Newgard, and in an article by G. L. Pressman and P. M. Newgard entitled "A Transducer for the Continuous External Measurement of Arterial Blood Pressure" (IEEE Trans. Bio-Med. Elec., Apr. 1963, pp. 73–81).

In a typical tonometric technique for monitoring blood pressure, a transducer which includes an array of pressure sensitive elements is positioned over a superficial artery, and a hold-down force is applied to the transducer so as to flatten the wall of the underlying artery without occluding the artery. The pressure sensitive elements in the array have at least one dimension smaller than the lumen of the underlying artery in which blood pressure is measured, and the transducer is positioned such that more than one of the individual pressure-sensitive elements is over at least a portion of the underlying artery. The output from one of the pressure sensitive elements is selected for monitoring blood pressure. One method for selecting the pressure sensitive element for monitoring blood pressure is disclosed in the above mentioned U.S. Pat. No. 4,269,193 issued to J. S. Eckerle. In addition, an improved method for selecting the correct pressure sensitive element for measuring blood pressure is disclosed in a patent application entitled "Active Element Selection for Continuous Blood Pressure Monitor Transducer" filed on even date herewith.

One of the difficulties encountered in prior systems for employing tonometric techniques for blood pressure measurement is the provision of an appropriate pressure source for creating the hold down pressure necessary to bring the sensor into contact with the patient's arm and to optimally flatten the underlying artery. In particular, prior designs based on conventional pump assemblies create pressure transients which tend to interfere with the operation of the pressure sensing elements. In addition, conventional pressure sources tend to be difficult to control, thus making it difficult to maintain a constant hold down pressure for the tonometer transducer. The pressurization system of the present invention, described in greater detail below overcomes these difficulties.

SUMMARY OF THE INVENTION

The present invention provides a pressurization source which can be used to provide hold down pressure to a tonometric transducer assembly which is used to measure blood pressure in a superficial artery. The system provided by the present invention is broadly comprised of a pressure source having first and second pressure chambers. Each of the pressure chambers is alternately in fluid communication with the transducer pressure chamber by means of a motorized drive mechanism which operates the pressure source and simultaneously controls the flow of air by means of a switching mechanism. A detachable connector assembly is utilized to permit simultaneous interruption of air flow and the electrical circuit of the system.

DETAILED DESCRIPTION OF THE PREFERRED EMBODIMENT

Figure 1:
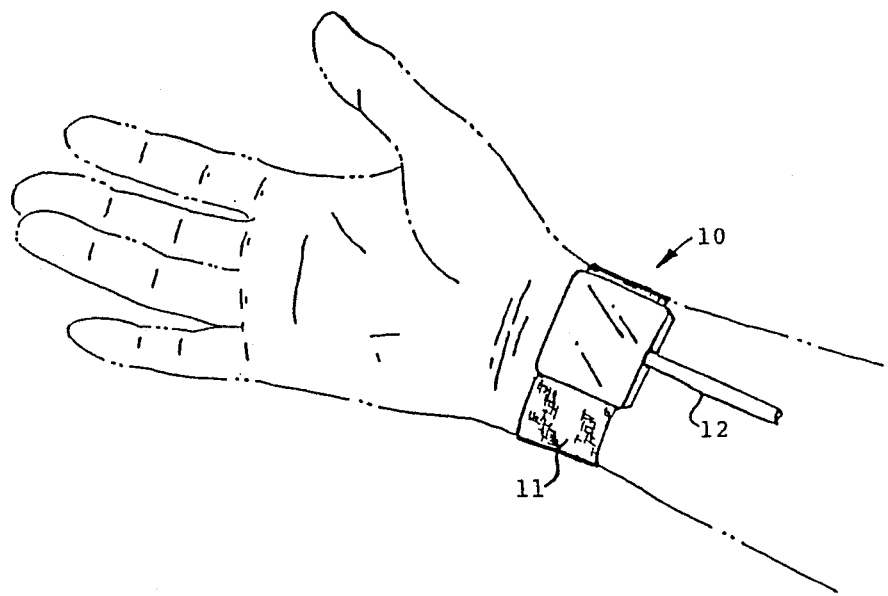
FIG. 1 is a view of the continuous blood pressure monitoring transducer of the present invention attached to a patient's wrist at a position overlying the radial artery.

Reference is now made to FIG. 1 wherein a continuous blood pressure monitor transducer 10 is shown attached to a patient's wrist at a point overlying the radial artery. The transducer is attached by means of a strap 11 in a manner similar to a conventional wristwatch. A cable assembly 12 connected to the transducer contains electrical cables for carrying electrical signals to and from the transducer. The cable assembly 12 also contains a pneumatic tube for providing pressurized air to a pressurizable bladder in the interior of the transducer in order to bring a sensor into contact with the patient's skin in a manner described in greater detail hereinbelow.

For the transducer to properly measure blood pressure it is important that the underlying artery be partially compressed. Specifically, it is important that the artery be flattened by a plane surface so that the stresses developed in the arterial wall perpendicular to the face of the sensor are negligible. This generally requires that the blood pressure measurement be taken on a superficial artery which runs over bone, against which the artery can be flattened.

Figure 2A:
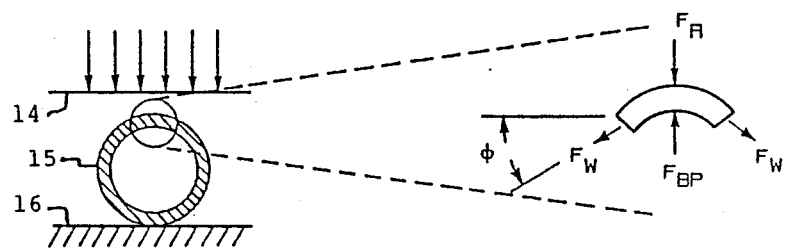
FIG. 2a is an illustration of force balance conditions for a sensing element positioned over a superficial unflattened artery.
Figure 2B:
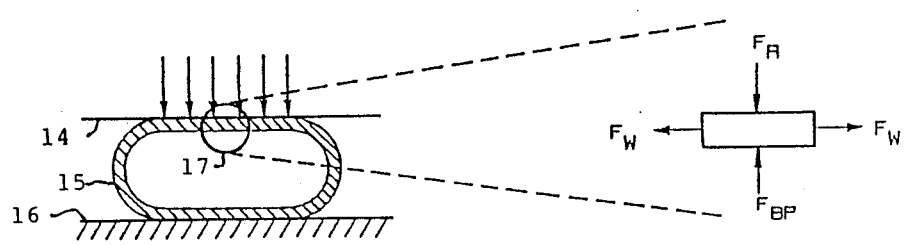
FIG. 2b is an illustration of force balance conditions for a sensing element positioned over a superficial artery which has been partially flattened.

FIGS. 2a and 2b illustrate stresses in the wall of a superficial artery such as the radial artery of the wrist. In FIG. 2a, the force balance on a small segment of arterial wall is illustrated for an unflattened artery. In this illustration, a sensor 14 is shown exerting a compressional force against an artery 15. The artery 15 overlies a bone 16, which is illustrated with a ground symbol. In this illustration, $F_R$ represents the reaction force which is measured by the sensor; $F_W$ is the force due to stresses in the artery wall; and $F_{BP}$ is the force developed by blood pressure in the artery. The artery behaves much like an ideal membrane, supporting only tensile stresses tangent to its surface. Thus, the angle, $\phi$, of the $F_W$ vector is as shown in FIG. 2a. Specifically, $\phi$ is nonzero for an unflattened artery. This wall stress reduces the amount of stress transmitted through the tissue to the surface of the tonometer sensor 14. Thus, the pressure (normal stress) measured by the sensor at the skin surface is lower than the actual blood pressure. This condition can be seen by summing the Y-direction force components shown in FIG. 2a:

$$\text{Sum}(F_Y) = 0 \rightarrow F_R = F_{BP} - 2F_W \sin \phi$$

As can be seen, the force measured by the sensor is lowered by the subtractive effect of the vertical components of the wall forces.

When the artery 15 is flattened, as shown in FIG. 2b, any stresses developed in the arterial wall are normal to the stresses transmitted to the sensor and do not affect the forces measured by the tonometer sensor. Therefore, in FIG. 2b, the force measured by one element of the tonometer sensor will be simply equal to the intraarterial blood pressure times the area of the sensor element.

Another important criterion in a measurement of this type is that the sensor measure pressure only over that portion of the artery wall which is flattened. Typically, the underlying artery is flattened over a wider region than the size of a single sensor element. Therefore, the sensor element which happens to be placed over this narrow region where accurate blood pressure readings can be taken must be selected by parts of the tonometer control system which are not directly related to the present invention and, therefore, are not discussed herein. This preferred measurement region is illustrated generally by reference number 17 in FIG. 2b.

Figure 3A:
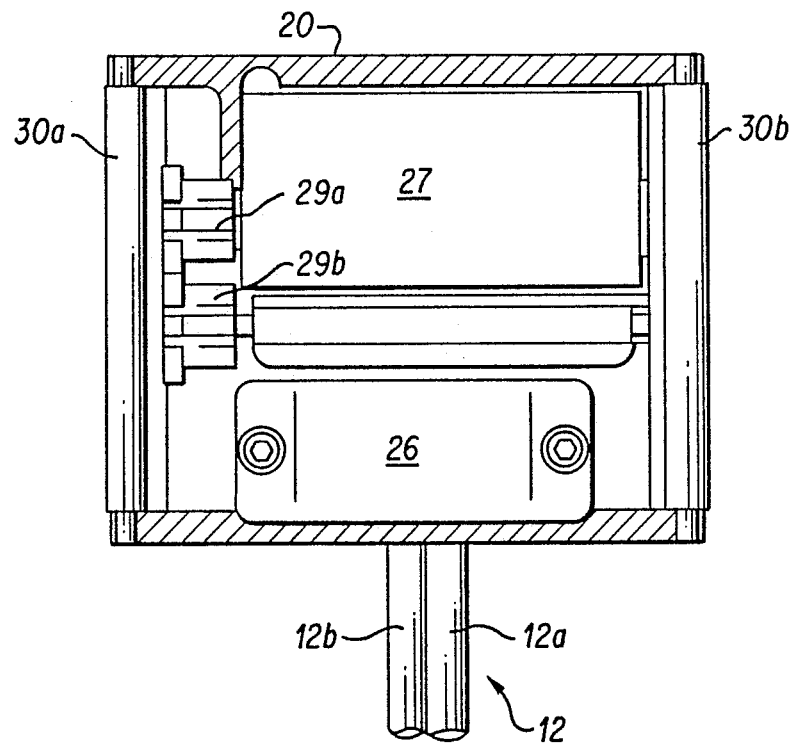
FIG. 3a is a top plan view of the continuous pressure monitor transducer of the preferred embodiment.
Figure 3B:
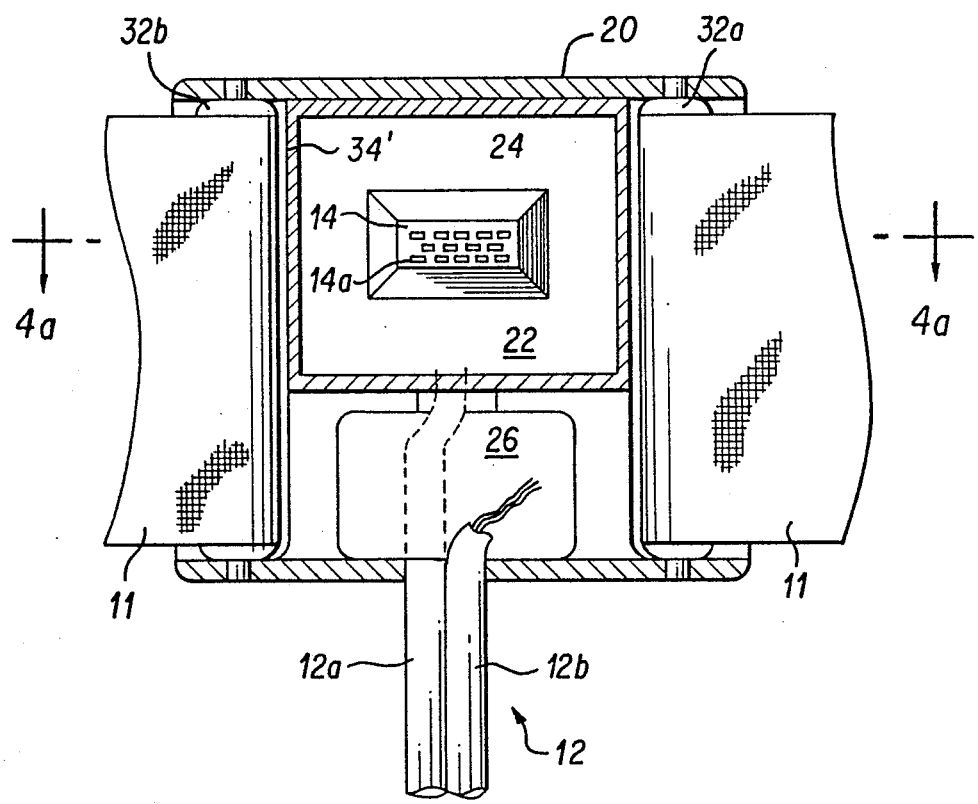
FIG. 3b is a bottom plan view of the continuous blood pressure monitor transducer of the preferred embodiment.
Figure 4A:
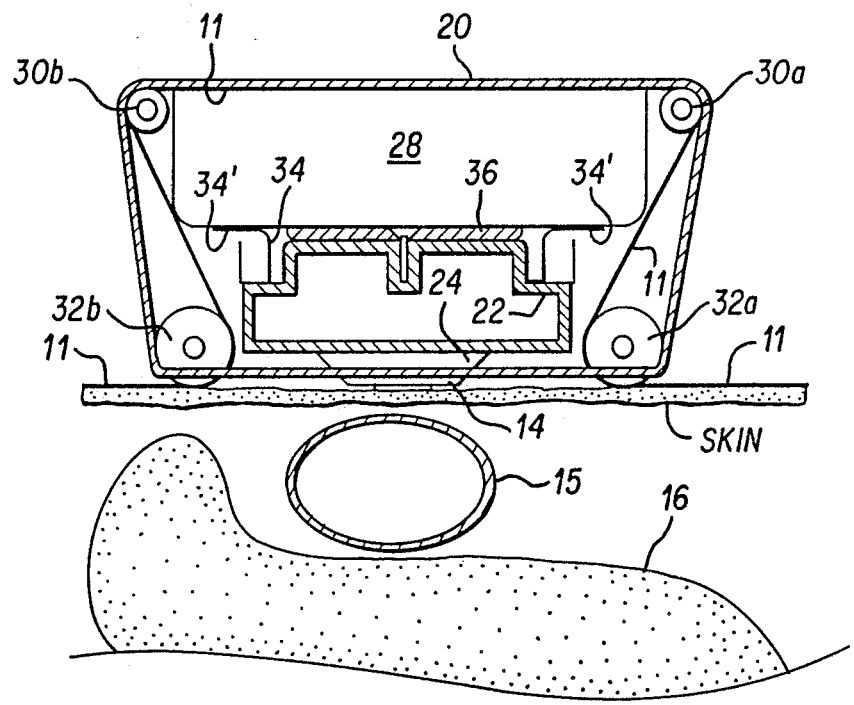
FIG. 4a is a cross sectional view of continuous blood pressure monitoring transducer of the present invention positioned on a patient's wrist with the sensor piston in the retracted position.
Figure 4B:
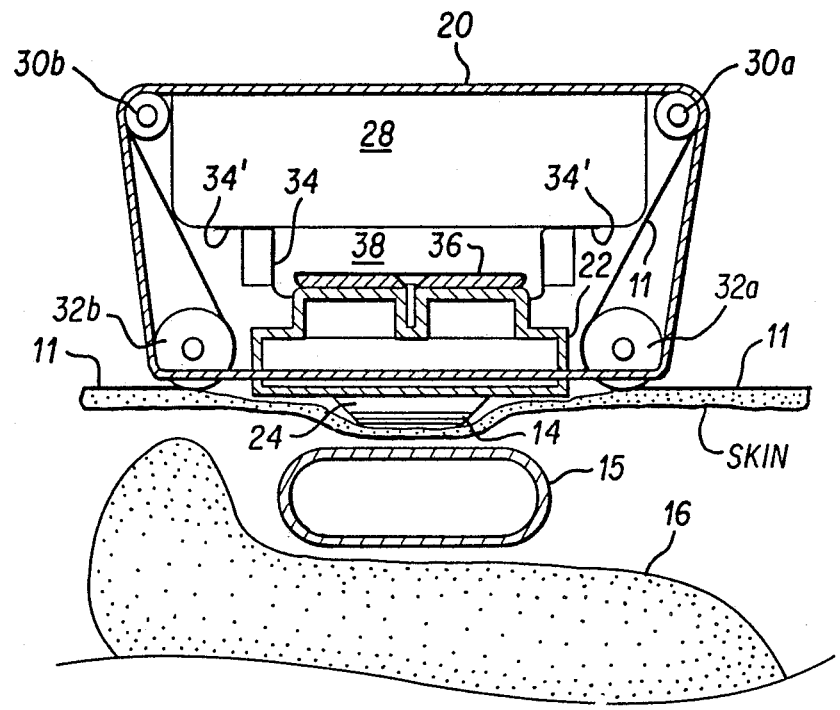
FIG. 4b is a cross sectional view of continuous blood pressure monitoring transducer of the present invention positioned on a patient's wrist with the sensor piston in the extended position.

Details relating to the continuous blood pressure transducer can be seen by referring to the top and bottom plan views shown in FIGS. 3a and 3b, respectively, and to the cross sectional side views shown in FIG. 4a and 4b. Referring to FIG. 3a, the transducer is comprised of an outer housing 20 containing a positioning system comprising a positioning motor 27 which drives a gear assembly comprising gears 29a and 29b. The positioning system moves the transducer along a path defined by a strap 11 (not shown) which is routed over a system of rollers 30a, 30b, 32a and 32b to maintain the transducer assembly properly positioned over the underlying artery. Operation of the system of the present invention can be understood without a detailed description of the aforementioned positioning system. The components shown in FIG. 3a are illustrated only for the purpose of providing orientation.

Referring to the bottom plan view of FIG. 3b, the transducer assembly is shown to include a sensor piston assembly 22 having a sensor mounting platform 24 on which the sensor 14 is mounted. The cable assembly 12 is received in a terminator cavity 26 which contains appropriate mounting terminals for the sensor electronics for monitoring the electronic signals within the transducer. The cable 12 contains an electrical cable bundle 12b and a pneumatic tube 12a. The electrical cable bundle 12b is connected to the mounting terminals contained in the terminator cavity 26. The pneumatic tube 12a is routed through the terminator cavity 26 to the pressurizable bellows, described in greater detail below, to cause movement of the sensor piston assembly 22.

FIG. 4a is a cross sectional view taken along section lines 4—4 of FIG. 3b showing the continuous blood pressure transducer positioned above a superficial artery 15 of a patient. The motor mechanism 27 for controlling the position of the transducer is contained in a motor housing 28. The motor mechanism is operably connected to the strap 11 which is routed over a system of rollers comprising upper rollers 30a and 30b and lower rollers 32a and 32b, respectively. For purposes of the present discussion, it is assumed that the transducer is properly positioned over the artery and, therefore, the details of operation of the motorized positioning mechanism are not discussed herein. The sensor piston 22 contains the electronic circuitry and wiring for the sensor 14. Again, details relating to the circuitry for the sensor 14 are not essential to an understanding of the operation of the pneumatic pressurization system of the present invention and, therefore, are not discussed in detail herein. However, a discussion of the operation of such a system can be found in U.S. Pat. No. 4,269,193, issued to Eckerle, which by this reference is incorporated for all purposes. In addition, an improved method for selecting the proper force sensing element is disclosed in a patent application entitled "Active Element Selection for Continuous Blood Pressure Monitor Transducer," filed on even date herewith.

Referring again to FIG. 4a, a flexible silicone rubber roller diaphragm 34 is shown with its perimeter attached to the lower surface of the motor housing 28 and is further secured to the top of the sensor piston 22 by means of a plate 36. The sealed perimeter portion of the diaphragm is illustrated by reference number 34' in FIG. 3b and FIGS. 4a and 4b. Both of the above mentioned attachments of the diaphragm 34 provide air tight seals. With the diaphragm 34 attached to the lower face of the motor housing 28 and the upper surface of the transducer piston assembly as described above, a pressurizable chamber 38 is formed within the transducer housing assembly. Since the flexible rubber bellows 34 is sealed both to the transducer piston 22 and to the lower face of the motor housing 28, pressurized air introduced into the pressurizable cavity 38 causes the transducer piston 22 to be pneumatically loaded. As the pressure in the cavity 38 is increased the transducer piston assembly 22 will be forced downward from the position shown in FIG. 4a to the position shown in FIG. 4b. The pneumatic pressure applied inside the rubber bellows 38 may be adjusted to supply the compressional force required to provide the necessary flattening of the artery wall, thus allowing the device to meet the flattening criteria described above in connection with FIG. 2b. Furthermore, the pressure source of the present invention can be used to provide a constant pressure to maintain the artery in an optimally flattened position.

When the transducer case is held in place on the wrist, generally over the radial artery, as shown in FIG. 1, the transducer piston 22 is thus supported over the radial artery by the rubber bellows, air pressure inside the bellows holds the sensor 14 and its supporting structure, against the skin surface with sufficient force to achieve the desired degree of flattening of the wall of the artery. Therefore, the individual force sensing elements in the sensor will produce output signals which accurately track the pulse waveform in the underlying artery.

Figure 5:
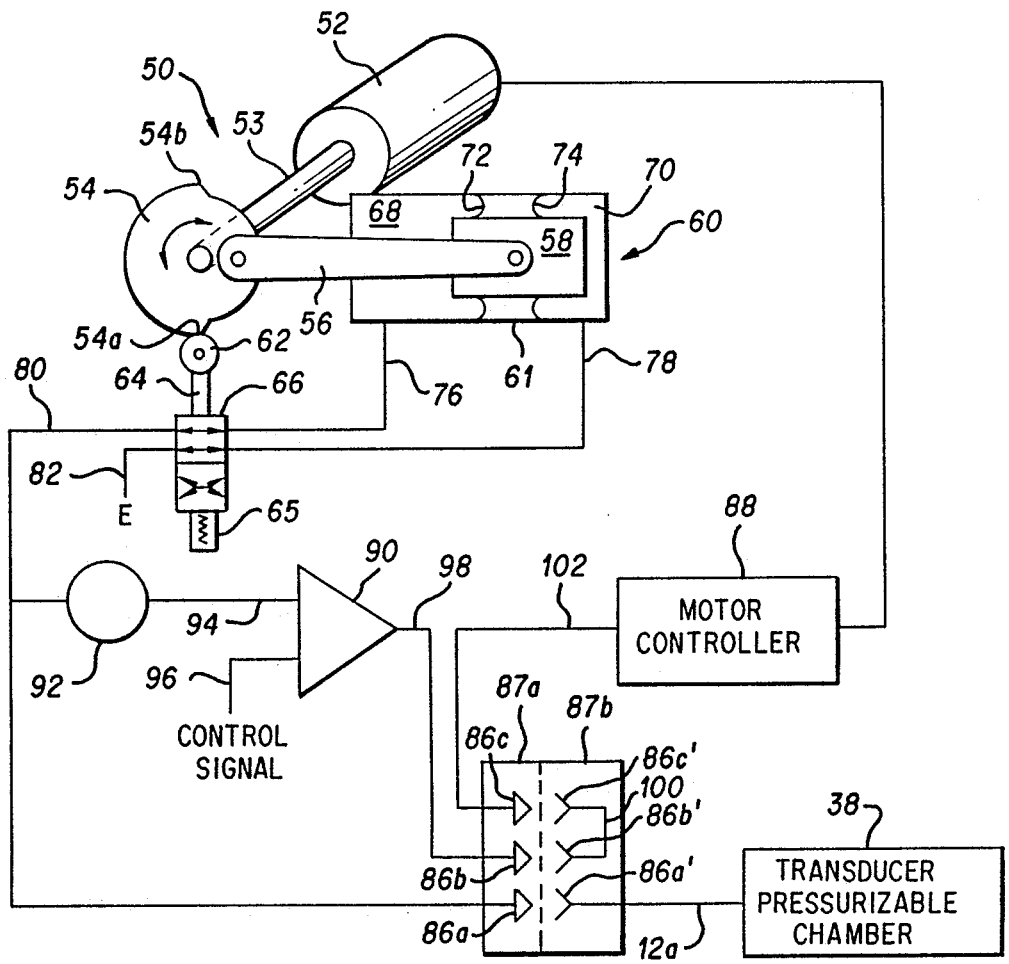
FIG. 5. is a system block diagram of the pressurization system of the present invention.

Referring to FIG. 5, a system block diagram is shown of the preferred embodiment of the pressurization system 50 of the present invention. A servo motor 52 having a shaft 53 with a cam 54 attached thereto operates to move a crank shaft 56 and associated piston 58 in a dual chamber pressure source 60. The cam 54 is also operatively engaged with a roller 62 which is attached to an actuator shaft 64 of a 4-way spool valve 66. The 4-way spool valve 66 includes a biasing means 65, which can be a conventional spring, which urges the roller 62 on the actuator shaft 64 into contact with the cam 54. First pressure chamber 68 is defined by one end of housing 61 and a first rolling diaphragm 72 which is secured to the inner face of the pressure source housing 61 and to one face of the piston 58. Similarly, second pressure chamber 70 is defined by the opposite end of housing 61 and a second rolling diaphragm 74 which is secured to the inner face of the pressure source housing 61 and to the opposite face of the piston 58. Rotation of the cam 54 controls the movement of the piston 58 and thus controls the compression in the pressure chambers 68 and 70. In addition, the angular position of the cam 54 controls the position of the actuator shaft 64 of the 4-way spool valve 66.

Gas is transported into and out of the first pressure chamber 68 by means of a first pneumatic line 76. Similarly, gas is transported into and out of the second pressure chamber 70 by means of a second pneumatic line 78. Each of the above mentioned pneumatic lines 76 and 78 are connected to ports on the 4-way spool valve 66. The position of the spool in spool valve 66 determines whether the respective pneumatic lines are in fluid communication with pneumatic line 80 or with the exhaust port 82. The pneumatic line 80 is connected to an appropriate pneumatic connector fitting 86a in connector assembly 87 to provide pressurized gas to pneumatic line 12a which further provides the pressurized gas to the transducer pressurizable chamber 38. Operation of the pressurization system 50 of the present invention is controlled by a motor controller 88 which is responsive to a control signal generated by a differential amplifier 90. A pressure transducer 92 is connected to pneumatic line 80 and generates an electrical signal which is proportional to the pressure in line 80. This electrical signal is provided to a first input terminal 94 of the differential amplifier 90. A control signal is provided to a second input terminal 96 of the differential amplifier. The output signal produced at the output terminal 98 of the differential amplifier will be an "error" signal representing the difference between the desired pressure and the actual pressure in the pneumatic line 80. The output terminal 98 of the differential amplifier is connected to an appropriate electrical connector fitting 86b in connector in the first portion 87a of connector 87. The input terminal 102 of the motor controller is connected to an appropriate electrical connector 86c in the first portion 87a of connector 87. Electrical connection between the terminals 98 and 102 is accomplished by a wire 100 which is connected to electrical connectors 86b' and 86c' in the second portion 87b of the connector assembly 87. When the first and second portions 87a and 87b of connector 87 are separated, there is a simultaneous interruption of the flow of gas to the pressurizable chamber 38 and the control signal to the motor controller 88.

Operation of the pressurization system of the present invention can be understood by referring to the system block diagram shown in FIG. 5. The servo motor 52 can be controlled to move in either the clockwise or the counter clockwise direction, as indicated by the arrows on cam 54. If the cam is rotated in the counter clockwise direction from the position shown in FIG. 5, the spool of the 4-way spool valve 66 will be in the position shown in FIG. 5. As the cam continues to rotate in the counter clockwise direction, the piston 58 will move toward the left, thus causing compression in first pressure chamber 68 of the pressure source 60. The pressure will be communicated through pneumatic line 76 to pneumatic line 80 and through connector 87 to pneumatic line 12a, thus providing pressurized gas to the transducer pressurizable chamber 38. As the cam 54 continues to rotate, the edge of the lobe 54b will eventually pass the roller 62, thus causing the actuator shaft 64 to be withdrawn, thereby switching the spool from the position shown in FIG. 5 to a position wherein pneumatic line 76 is connected to the exhaust port 82 and pneumatic line 78 is connected to pneumatic line 80. This switching occurs when the piston is at top dead center in relation to the compression cycle for the first pressure chamber 68. Continued movement of the cam in the counter clockwise direction will cause the piston 58 to begin moving toward the right to define a compression cycle in second pressurization chamber 70. Thus it can be seen that the switching arrangement defined by the cam and spool valve combination of FIG. 5 will always connect the pressure chamber which is being compressed to the pneumatic lines which will communicate the compressed gas to the pressurizable chamber 38. Furthermore, it is important to note that the switching of the spool valve 66 always occurs when the piston is at top dead center with respect to the respective pressure chamber. In particular, the switching occurs at a point for which the angular movement of the cam is a maximum and the axial movement of the piston is a minimum. This allows the system to provide pressurization with a minimum amount of pressure transients being communicated to the pressurizable chamber 38. The pressurization source of the present invention, therefore, prevents such undesired pressure transients from being communicated to the pressure sensing elements on the sensor assembly, thereby insuring maximum accuracy in the blood pressure measurement. For rapid pressurization of the pressurizable chamber 38, the servo motor 52 can be controlled by the motor controller 88 to rotate continuously in the counter clockwise direction until the desired pressure is reached in the pressurizable chamber 38. Once the desired pressure has been reached, minor changes in pressure can be made by rotating the cam 54 through a relatively small angle, thus causing minor changes in pressure in the chamber 38. The relative volumes of the first and second pressure chamber 70 and the volume of the pressurizable chamber 38 can be chosen so that maximum control is maintained over small pressure changes after the optimum hold down pressure has been achieved.

Although the method and apparatus of the present invention has been described in connection with the preferred embodiment, it is not intended to be limited to the specific form set forth herein, but on the contrary, it is intended to cover alternatives and equivalents as may reasonable be included within the spirit and scope of the invention as defined by the appended claims.

I claim:

1. A pressurization system for a continuous blood pressure monitor transducer, comprising:

a transducer having a pressurizable chamber;

compression means for compressing a fluid having first and second compression chambers, said first and second chambers being alternately in fluid communication with said pressurizable chamber within said transducer;

switch means operatively connected to said first and second chambers and said pressurizable chamber for controlling fluid flow between said first and second chambers and said pressurizable chamber; and means operatively connected to said compression means and said switch means for driving said compression means and simultaneously operating said switch means to provide pressurized fluid into said pressurizable chamber.

2. The pressurization system according to claim 1, wherein said means for driving comprises a motor driven cam in operative engagement with said compression means and said switch means.

3. The pressurization system according to claim 1, further comprising detachable connector means operatively connected to said pressurizable chamber and to said means for driving for interrupting fluid flow to said pressurizable chamber and simultaneously deactivating said means for driving when said detachable connector means is detached.

4. A pressurization system for a continuous blood pressure monitor transducer, comprising:

a transducer having a pressurizable chamber, said transducer adapted to be positioned over an artery;

compression means for compressing a fluid having first and second compression chambers, said first and second chambers being alternately in fluid communication with said pressurizable chamber within said transducer;

switch means operatively connected to said first and second chambers and said pressurizable chamber for controlling fluid flow between said first and second chambers and said pressurizable chamber; and means operatively connected to said compression means and said switch means for driving said compression means and simultaneously operating said switch means to provide pressurized fluid into said pressurizable chamber to maintain said underlying artery in an optimally flattened condition.

5. The pressurization system according to claim 4, wherein said means for driving comprises a motor driven cam in operative engagement with said compression means and said switch means.

6. The pressurization system according to claim 5, further comprising:

means for sensing the pressure in said pressurizable chamber, said means for sensing being operatively connected to said pressurizable chamber and producing a first signal responsive to said pressure in said pressurizable chamber;

means for comparing said said first signal with a predetermined control signal responsive to a desired pressure, said means for comparing being operatively connected to said means for sensing; and means for generating an output signal responsive to said first signal and said control signal and operatively connected to said means for driving to cause said means for driving said compression means to change said pressure in said pressurizable chamber responsive to said output signal.

7. The pressurization system according to claim 6, said pressurizable chamber comprising a flexible silicone rubber roller diaphragm.

8. The pressurization system according to claim 7, further comprising detachable connector means operatively connected to said pressurizable chamber and to said means for driving for interrupting fluid flow to said pressurizable chamber and simultaneously deactivating said means for driving when said detachable connector means is detached .

* * * * *